United States Patent [19]

Chang

[11] 4,036,854

[45] July 19, 1977

[54] METHOD FOR PREPARING COUMARIN

[75] Inventor: Kuo Yuan Chang, Midland, Mich.

[73] Assignee: The Dow Chemical Company, Midland, Mich.

[21] Appl. No.: 680,244

[22] Filed: Apr. 26, 1976

Related U.S. Application Data

[62] Division of Ser. No. 555,472, March 5, 1975.

[51] Int. Cl.$^2$ .......................................... C07D 311/10
[52] U.S. Cl. ............................ 260/343.2 R; 210/274; 210/305
[58] Field of Search ................................ 260/343.2 R

[56] References Cited

U.S. PATENT DOCUMENTS 3,631,067   12/1971   Nankee et al. ................ 260/343.2 R

*Primary Examiner*—Lorraine A. Weinberger
*Assistant Examiner*—Jane T. Fan
*Attorney, Agent, or Firm*—Glwynn R. Baker

[57] ABSTRACT

A filter having a peripheral skirt extending above and below the filter element, provides a gaseous cushion which prevents clogging the filter. The peripheral edges of the filter may have means for preventing entry of solid in the narrow space between the skirt wall and the filter edge. The filter can be part of an entry or exit port in the base of a crystallizer in which crystals are formed, washed, melted and filtered in a single unit. A reactor containing the novel filter is also useful for carrying reactions using heterogeneous catalysts and reactions in which an initially homogeneous catalyst becomes nonhomogeneous during the reaction.

4 Claims, 3 Drawing Figures

METHOD FOR PREPARING COUMARIN

CROSS-REFERENCE TO RELATED APPLICATION

This is a division of application Ser. No. 555,472 filed Mar. 5, 1975.

BACKGROUND OF THE INVENTION

In the chemical industry one of the important ways of purifying materials is by crystallization. This process consists of super-saturating a solvent and effecting crystallization by cooling or evaporating additional solvent to form a slurry of desired crystals and mother liquor. Usually, the slurry is removed from a crystallization vessel, the mother liquor is separated by filtration or by centrifugation. The separated crystals are washed and then the purified product is recovered. This process requires repeated solids handling, in addition to multiple and varied pieces of equipment that need maintenance and attention. It would be desirable to carry out all the steps in one unit.

Some batch-type chemical reactions are carried out in liquid phase using a heterogeneous catalyst. In other instances the catalyzed reactions start as homogeneously catalyzed systems, but at completion of the reaction the catalyst is crystallized from the liquid, because its solubility in the product of the reaction is lower than the solubility in the starting ingredients. The catalyst is not spent and is reusable. However, for such catalytic reactions in the past, it has been necessary to drain a reactor, separate the solid catalyst from the liquid phase, wash and recover the catalyst and reload the reactor with the catalyst to repeat the reaction. Avoiding the necessity of removing the solid catalyst from and reloading to the reactor before repeating the reaction results in a much more efficient procedure than that of prior art operations.

SUMMARY OF THE INVENTION

This invention concerns a filter structure having a filtering element, a skirt extending around the periphery of and above and below the filter element, defining a space for an inert gas, and means for feeding said inert gas against a surface of the filter to substantially avoid clogging said filter. The invention also concerns a vessel having the above described filter element at its base, for crystallization and washing crystals in a single unit or for running liquid phase catalytic reactions wherein the catalyst remains solid throughout the reactor (e.g. reactions with heterogeneous catalysts) or wherein the catalyst is soluble at the beginning of the reaction period but is solid at the end of the reaction. The catalyst remains in the reactor for reuse, but liquid products are filtered and drained.

DETAILED DESCRIPTION OF THE INVENTION

Figure 1:
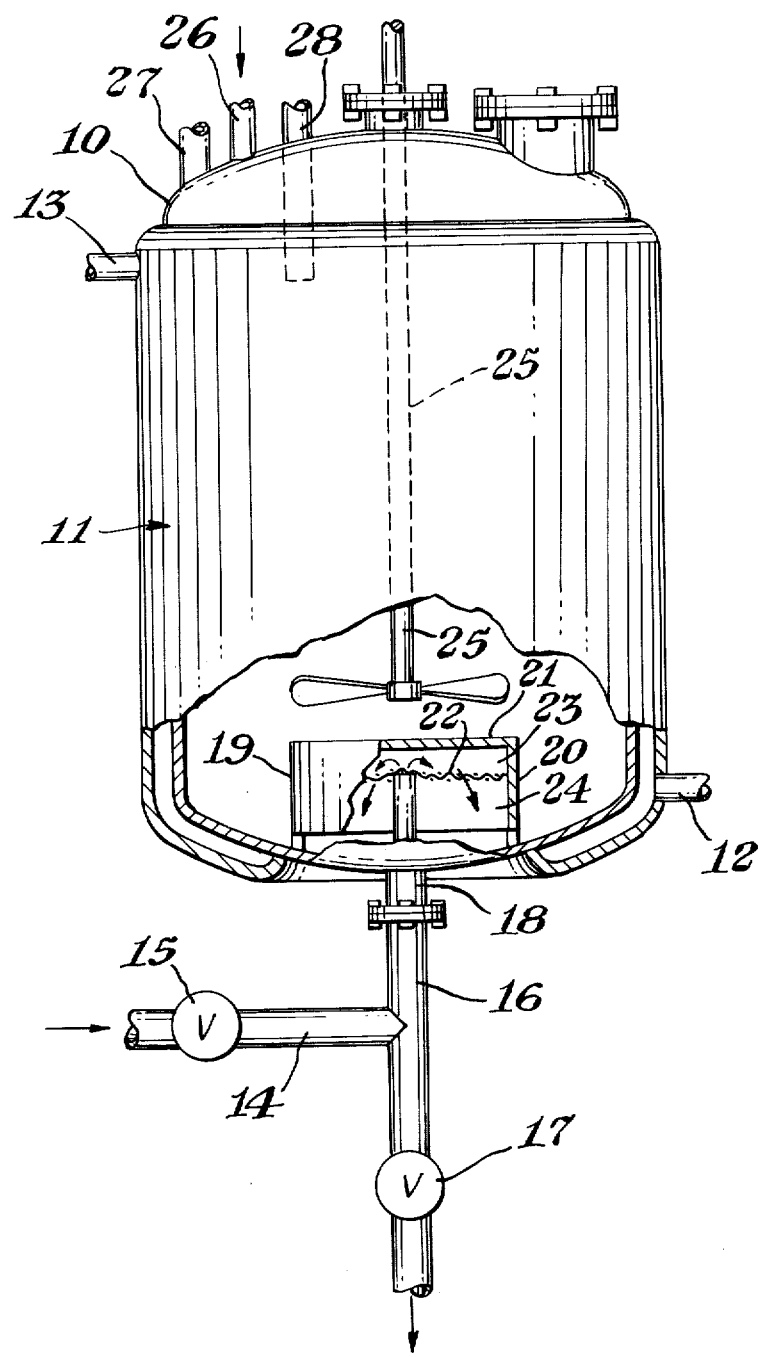
FIG. 1 is a vertical section of a reactor or vessel having a filter structure in its base, and means for draining the reactor through the bottom.

In FIG. 1, 10 is the wall of a reactor or vessel having a jacket 11, with an inlet 12 and outlet 13 for feeding a heat exchange material through the jacketed portion of the vessel. Conduit or pipe 14, having a valve 15, connects with conduit 16. The latter has a valve 17 located below the junction with conduit 14. Conduit 16 is connected to conduit 18 which extends into the inside of the vessel base. The connection between conduits 16 and 18 can be through a weld, a through sleeve, or opposing flanged faces which are bolted or clamped together, with or without a gasket, to form a liquid fluid seal. A filter element 19 fits closely around the top of conduit 18 and extends outwardly therefrom to a peripheral skirt 20, which has an impervious top 21, to enclose the filter medium 22 in a tubular, liquid and gas impermeable, member defined by skirt 20 and top 21. One open space 23 between the filter member top 21 is thus provided. The distance between the bottom of skirt 20 and the wall of the vessel can be adjusted so that it is less than the size of catalyst particles or crystals when the latter are formed in the vessel.

The filter medium, preferably, should fit snugly against the inside wall of the skirt or if the filter medium is a metal screen it can be welded to the skirt, to thereby avoid entrapment of fine particles between the filter medium and skirt wall. Any entrapment of fine particles serves as a potential source of reduced effectiveness of the filter because of the possibility that such particles can act as seed for crystallization or as an area in which accretion of particles can take place. An alternative way of mitigating entrapment of particles between the filter medium and the skirt is by use of a retaining ring having notched support legs. Such a ring can extend around the inner periphery of the skirt and about tightly against it. The ring should have a central opening sufficiently large so as not to impede flow of gas or liquid through the filter medium. Thus, a second open space 24, defined by the bottom of the filter medium, the skirt wall and the bottom of the vessel is formed.

The vessel is preferably, but not necessarily fitted with a stirrer 25, an opening 26 for feeding a crude product or a reactant or catalyst and a thermocouple well 27. Another optional opening 28 in the top of the vessel can be a connection to a distillation column or a condenser (not shown).

Figure 2:
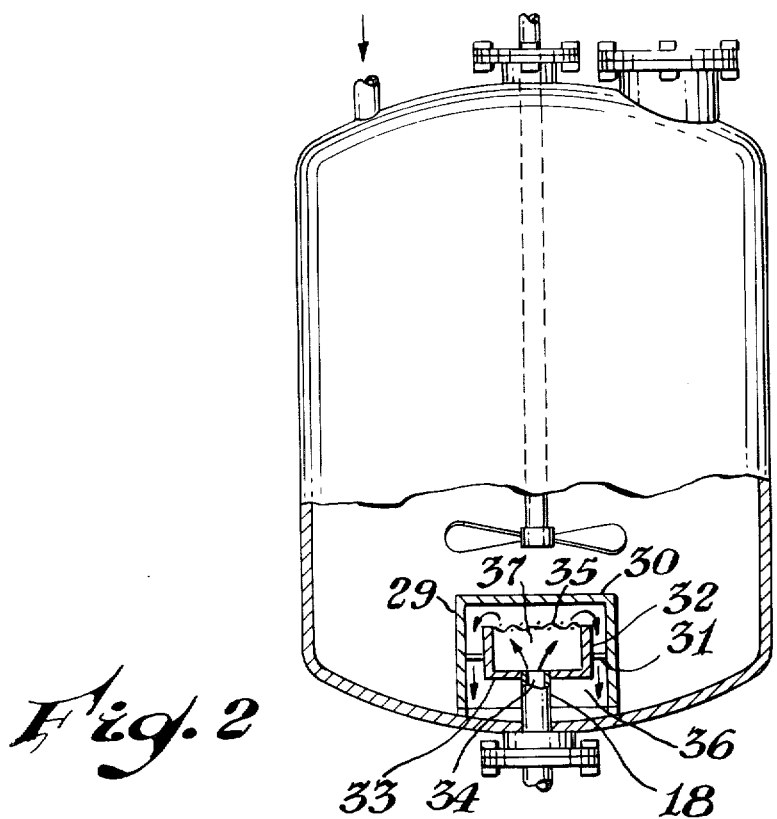
FIG. 2 is a vertical section of a modified form of the filter structure, which can be placed in the reactor shown in FIG. 1.

FIG. 2 shows a modification of the invention, which also is located in the base of a reactor of the type disclosed in FIG. 1. Valved lines 14, 16 and 18 are present in this modification. Line 18 is connected to a filter structure inside of and near the base of a reactor. The filter structure is confined in a housing which comprises an imperforate, vertical peripheral wall 29, an imperforate top 30 connected to wall 29, and laterally projecting spaced ribs 31 which abut against a vertical, imperforate wall 32 of a filter holding structure. The wall 32 is connected to a base 33 with a central opening 34. Mounted on wall 32 is a filter element 35, which is shown in the drawing as a screen, but as pointed out above, it can be any well known filtering medium. The vertical wall 29 is somewhat longer than wall 32 thereby providing open space 36, which can serve as a pocket for an inert gaseous fluid which tends to prevent entry of solids onto the surface of the filter element 35. Another pocket 37, defined by wall 32 and filter element 35, serves as an area in which a gaseous fluid is retained. The pocket 37 also serves to hold gas in the event of compression in the reaction zone.

Figure 3:
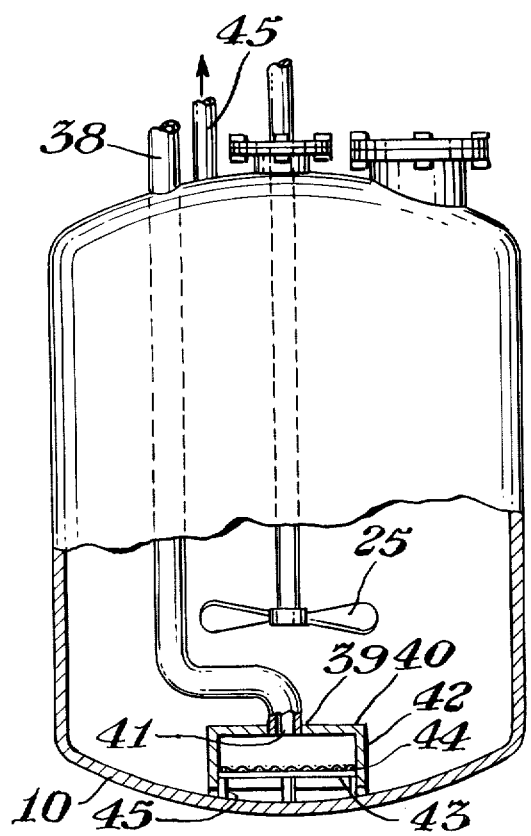
FIG. 3 is a vertical section of another variation of the filter structure showing means for feeding an inert gas and removing liquid products through an upper portion of the reactor.

FIG. 3, shows another modification of the invention in a vessel similar to that of FIG. 1. In this modification the novel filter has a tubular member 38, fitted in a sleeve 39 in an opening in the top of the filter reactor. The tubular member 38 extends downwardly and inwardly and terminates near the base of the reactor at about the center of said base, and below stirrer 25. Tubular member 38 is connected to a laterally extending plate 40 having a central opening 41. The plate is otherwise impervious to the passage of fluids. Connected to plate 40 is a peripheral vertical skirt 42, which is also impervious to fluids. The bottom of skirt 42 is closely spaced from the bottom of reactor wall 10. Spaced intermediate the plate 40 and the bottom of skirt 42 is a filter element 43. Thus, the filter element is enclosed within a casing defined by skirt 42 and plate 40. The filter element covers substantially the entire area between the inner walls of skirt 42. The filter medium can be a metal screen, paper, cloth or other well known filtering medium. If desired a support ring 44 which extends around the entire periphery of skirt 42 can be used to keep the filter medium in place and to prevent entry of fines between the skirt wall and the periphery of the filter. Such a support ring can also be used in the modifications shown in FIGS. 1 and 2. The support ring has a vertical member 45 which extends below the skirt 42, and is preferably notched to provide means for flow of liquid, but the notches are fine enough to prevent entry of solids from the vessel into spaces, thus leaving the filtering surfaces substantially unobstructed during use.

The operation of the system as a crystallizer-purifier is described using any of the above filter structures. A crude naphthalene stream obtained as still bottoms from cracking a naphtha to produce light olefins such as ethylene and propylene is fractioned to provide still bottoms containing 50% or more of naphthalene. This naphthalene mixture is fed to the reactor hot and as a liquid. It is cooled in the reactor with gentle stirring to a temperature below 80° C. and preferably to about 50° C. by passing cooling water through the jacket of reactor 10. During the crystallization period the valve in line 14 is open sufficiently to force a stream of air through the filter and preferably to bubble air through the crystallizing mixture. Valve 17 is closed during this stage. The passage of the stream of air through the filter prevents any crystals from entering the spaces between the filter skirt and reactor wall.

After crystallization is completed the valve in line 14 is closed and valve 17 is open. The mother liquor is then drained through line 16. The latter can be connected to a vacuum line, if desired, to speed withdrawal of mother liquor. After draining mother liquor, the valve 17 is closed, a wash liquid, such as ethanol is introduced into the reactor through line 26 and the mixture is stirred. After washing, the wash liquid is drained by opening valve 17. When no further liquid flows through line 16, the valve is again closed, a heating medium is passed through the jacket of reactor 10 and the naphthalene is melted, and then withdrawn through line 16 by opening the valve 17. In this latter step, filtration and withdrawal of liquid occurs in the same operation. In addition, the ethanol which remained in the reactor after washing was substantially all removed by distillation during the melting and draining the purified naphthalene through the filter.

The reactors above are particularly adaptable for the preparation of coumarin by the process disclosed in U.S. Pat. No. 3,631,067 which is incorporated herein by reference. In this procedure, exemplified by the use of the filter element of FIG. 3, a mixture of about 1 mol of salicyladehyde, 0.2 to 0.6 mol of an alkali metal acetate, an example of which is sodium acetate, and 1 to 4 mols of acetic anhydride are fed into the reactor through line 38. Preferably, the acetic anhydride is added incrementally, so that about equimolar quantities with the salicylaldehyde are initially present in the reactor. The stirrer is started and the mixture is heated up to about 175°–180° C. As the reaction proceeds acetic acid which forms is distilled through line 45, to which a condenser (not shown) is attached. During the reaction nitrogen or other dry inert gas is fed through lines 17–18, and through the filter. Thus, a gas pocket is formed above and below filter element. Initially, the sodium acetate goes into solution in the reaction medium, but as the reaction proceeds its crystallizes from the mixture. The gas flow through the filter prevents entry of crystals onto the filter surface and as the crystals grow they become too large to enter the narrow space between the filter element skirt 42 and the reactor base. On completing the reaction, the liquid is withdrawn by opening valve 17 and drawing a vacuum on line 16. Since only a small amount of sodium acetate catalyst is lost, the reactor can be recharged with salicylaldehyde and acetic anhydride without removal of the catalyst from the reactor. In a run in which an initial charge of 100 parts by weight of sodium acetate, 244 parts salicylaldehyde and 204 parts acetic anhydride and incremental addition of 800 parts of the latter was made during reaction at a temperature of about 175° C. for about 6 hours, about 378 parts of acetic acid were distilled.

The reactor was drained in 0.8 minutes at 350 mm pressure at about 95° C. From 640 parts of the reaction mixture, which was distilled at 5 mm pressure, 110 parts by weight of crystalline coumarin were recovered. The reactor can be recharged with salicylaldehyde and acetic anhydride and the process for conversion of the reactants to coumarin is repeated. This can be done without removing the crystallized catalyst from the reactor and if desired, without previous washing of the catalyst.

I claim:

1. A method of preparing coumarin by reacting salicylaldehyde, 1 to about 4 moles of acetic anhydride per mole of salicylaldehyde and an alkali metal acetate wherein the molar concentration of the alkali metal acetate is at or below the concentration of salicylaldehyde in the reaction, said reaction being conducted at temperatures up to 200° C for between about 2 and about 10 hours, the improvement comprising draining the liquid contents of the reactor through a filter medium located at the base of the reactor while passing an inert gaseous medium through said filter, to thereby retain the crystalline alkali metal acetate in the reactor, adding salicylaldehyde and acetic anhydride to the reactor and repeating the conversion thereof to coumarin without prior removal of the alkali metal acetate from the reactor.

2. The method of claim 1 in which the alkali metal acetate is sodium acetate.

3. The method of claim 1 in which the acetic anhydride is added incrementally and acetic acid is distilled during the reaction.

4. The method of claim 3 in which a ratio of 100 parts by weight of sodium acetate, 244 parts by weight of salicylaldehyde and 204 parts by weight acetic anhydride is initially charged to the reactor and an additional 800 parts by weight of acetic anhydride are added incrementally during the reaction at a temperature of about 175° C.

* * * * *